(12) United States Patent
Linville et al.

(10) Patent No.: US 6,197,261 B1
(45) Date of Patent: Mar. 6, 2001

(54) MACHINE FOR OPENING BLOOD SEGMENTS

(76) Inventors: Richard A. Linville; Renée A. Linville, both of 7019 SW. 57 Rd., Alachua County, FL (US) 32608-4777

( * ) Notice: Subject to any disclaimer, the term of this patent is extended or adjusted under 35 U.S.C. 154(b) by 0 days.

(21) Appl. No.: 09/017,303

(22) Filed: Feb. 2, 1998

(51) Int. Cl.[7] ........................................ G01N 1/02
(52) U.S. Cl. .................. 422/104; 422/99; 422/100; 600/573; 600/576; 600/577
(58) Field of Search ................ 422/99, 102, 103, 422/104; 436/183; 600/573, 576, 577

(56) References Cited

U.S. PATENT DOCUMENTS

| | | | |
|---|---|---|---|
| D. 296,361 | 6/1988 | Gerich et al. | D24/147 |
| 4,176,451 | 12/1979 | McMorrow | 422/99 |
| 4,399,103 | 8/1983 | Ferrara | 436/180 |
| 4,790,842 | * 12/1988 | Coburn | 604/408 |
| 4,938,929 | * 7/1990 | Bost | 422/100 |
| 5,055,271 | * 10/1991 | Golias et al. | 422/99 |
| 5,173,265 | * 12/1992 | Golias et al. | 422/99 |
| 5,254,312 | 10/1993 | Staebler et al. | 604/414 |
| 5,320,811 | * 6/1994 | Mount et al. | 422/101 |
| 5,667,098 | * 9/1997 | Levine et al. | 222/1 |
| 5,714,125 | * 2/1998 | Sagstetter | 422/102 |

FOREIGN PATENT DOCUMENTS

0350792 * 1/1990 (EP) .

* cited by examiner

*Primary Examiner*—Long V. Le

(57) ABSTRACT

A machine for opening simultaneously a plurality of blood segments comprising a number of segment carriers laterally co-joined and having therein strictly located apertures, an attached needle guide having perforations aligned with the carrier apertures and a spring-returned handle assembly containing captive needles to the same number as, and aligned with, the carrier apertures and guide perforations. Activation of the handle forces the needles to penetrate all blood segments in the carriers. A base tray is provided to contain any possible leakage from the segments.

2 Claims, 3 Drawing Sheets

MACHINE FOR OPENING BLOOD SEGMENTS

BACKGROUND AND SUMMARY OF THE INVENTION

This invention relates to that class of devices used to open blood segment tubes as used by hospital blood banks and blood collection centers. Blood segments are short lengths of plastic tubing, sealed at each end, which contain a sample of whole human blood. An identification sticker is affixed to insure traceability. Medical laboratories routinely open blood segments to obtain a sample of blood, often in significant numbers and under time pressure.

The customary way of opening these segments is to cut them open with scissors and to use gauze to clean up the inevitable blood leakage. This leakage often results in glove contamination and work area contamination, the former of which necessitates disposal of the gloves, the latter of which necessitates extensive clean-up. After being opened, the segment is inserted into a test tube and is squeezed thereby forcing a few drops of blood into the tube for subsequent procedures.

Several devices now in use have been designed to alleviate the leakage problem and, in general, they do that very well. None, however, is capable of opening more than one segment at a time. There is, for example, a device called "HEMATYPE", patent pending by Medical Safety Products, Inc., Inglewood, Calif., which is identical in function, and only slightly different in form, from devices described in U.S. Pat. Nos. 4176451 and 5254312. As will be noted, these devices are to be placed into the open end of a test tube and a blood segment is to be forced downward onto a piercing means which opens the segment. The segment is then to be squeezed thereby forcing a blood sample into the test tube. The device is then discarded. Another device called "SEGSAFE", being produced by Alpha Scientific Corporation of Malvern, Pa., is, in essence, a small plastic test tube with an integral piercing means. Again, a blood segment is forced downward onto the piercing means, the segment is squeezed, and a sample is taken. This sample is retained within the device and procedures are done therein rather than being done in a separate test tube. Unfortunately, it is of a cloudy color which tends to impede visual evaluation of the tube's contents. This is, also, a throw-away item. U.S. Pat. No. 4399103 offers a different but somewhat cumbersome means of opening a blood segment.

Yet another very recent device, a machine called "SABER", patent originally applied for by SG Scientific, Inc. of Gainesville, Fla. is now being distributed by Gamma Biologicals, Inc. This machine is intended for long-term usage in that it contains an internal and integral means of cleaning the piercing needle. A segment is inserted into an opening in the machine, a plunger is pressed and released, and the segment is removed for processing. The machine is supposed to clean the needle. In this instance, placement of the identification sticker becomes important, sometimes necessitating removal and repositioning of the sticker. In any case, this machine, while not a disposable item, can open only one segment at a time and tends to produce some degree of blood leakage after several usages.

A disadvantage common to all the above described ways and means of opening segments is that much valuable technician time is lost in the simple mechanics of making an opening in a blood segment. The scissors method is by far the most prevalent and the most inefficient way of doing the job. The other means are certainly cleaner than the use of scissors but still they can open only one segment at a time when it is often needful to open ten or twenty segments as quickly as possible.

It is therefore an object of this invention to provide a machine and method to open cleanly, quickly, and simultaneously a plurality of blood segments. It is believed that, while this invention would have utility in any application requiring the opening of sealed plastic tubing segments containing fluid of any type, its greatest utility will be to blood bank laboratories.

SUMMARY OF THE INVENTION

The present invention seeks to provide a means of opening several blood segments simultaneously while reducing, if not eliminating, glove and work area contamination. In accomplishing this, the machine of the present invention provides for a number of holders, or carriers, which hold separate and align a number of blood segments. A handle means containing an equal number of piercing devices is provided which, upon activation, causes all of the piercing devices, aligned by a guide means, to penetrate all segments simultaneously, the holes thereby created being of such fineness that blood does not leak out by force of gravity alone. Segments are then removed and processed as usual. In the unlikely but possible event of blood leakage, the machine is mounted in a tray which would confine leakage to the machine only.

Additional benefits and advantages of the present invention will become evident to one skilled in the art to which this invention relates from the subsequent description of the various embodiments in conjunction with the accompanying drawings.

DETAILED DESCRIPTION OF THE PREFERRED EMBODIMENTS

Figure 1:
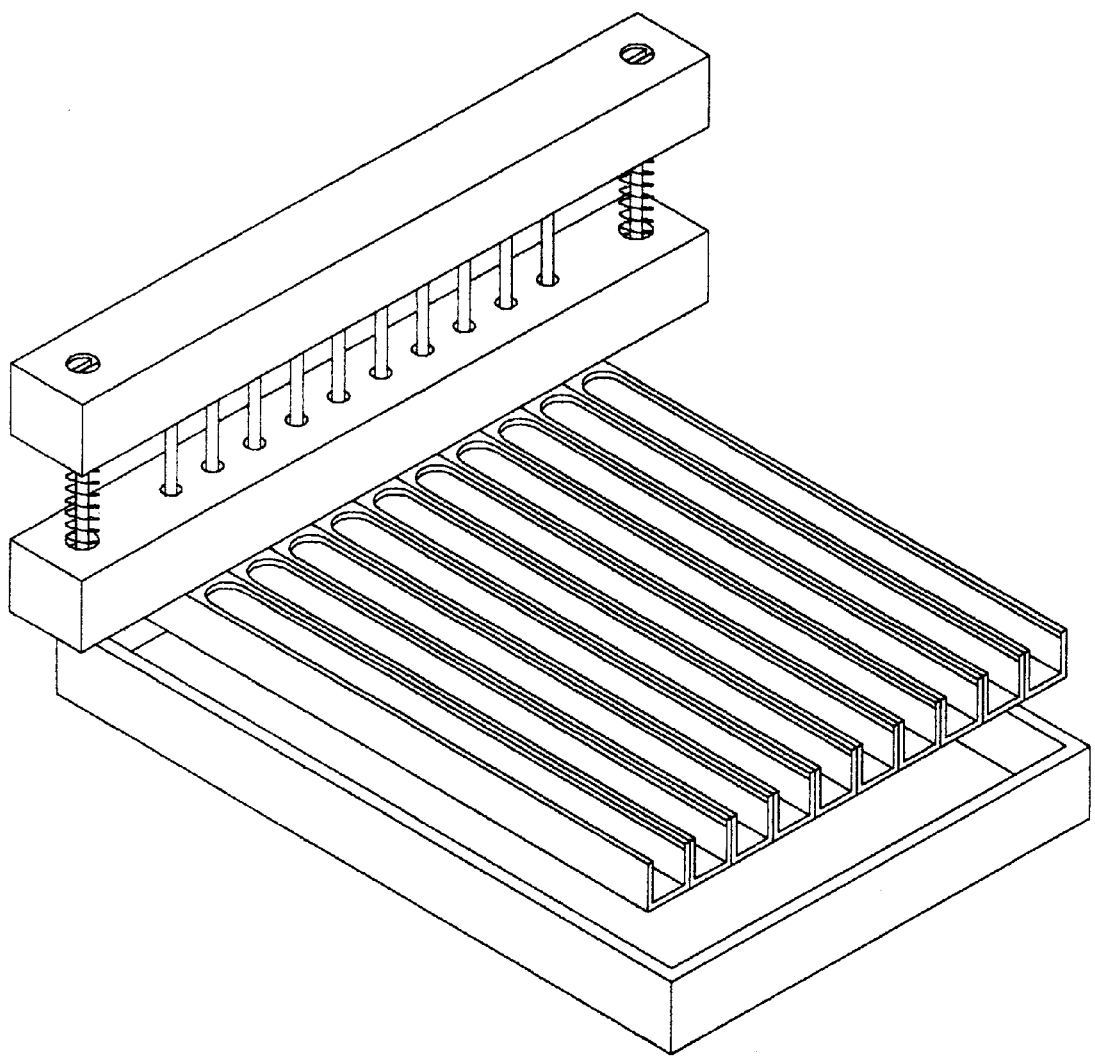
FIG. 1 is a perspective view of the preferred embodiment of the present invention.
Figure 2A:
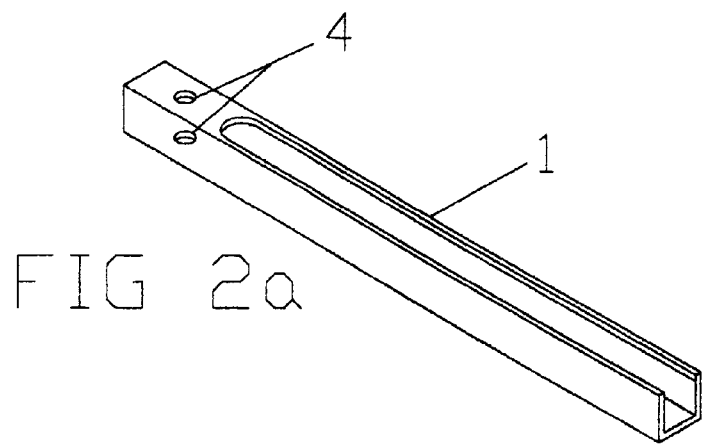
FIG. 2a is a perspective of a single carrier, preferred embodiment.
Figure 2B:
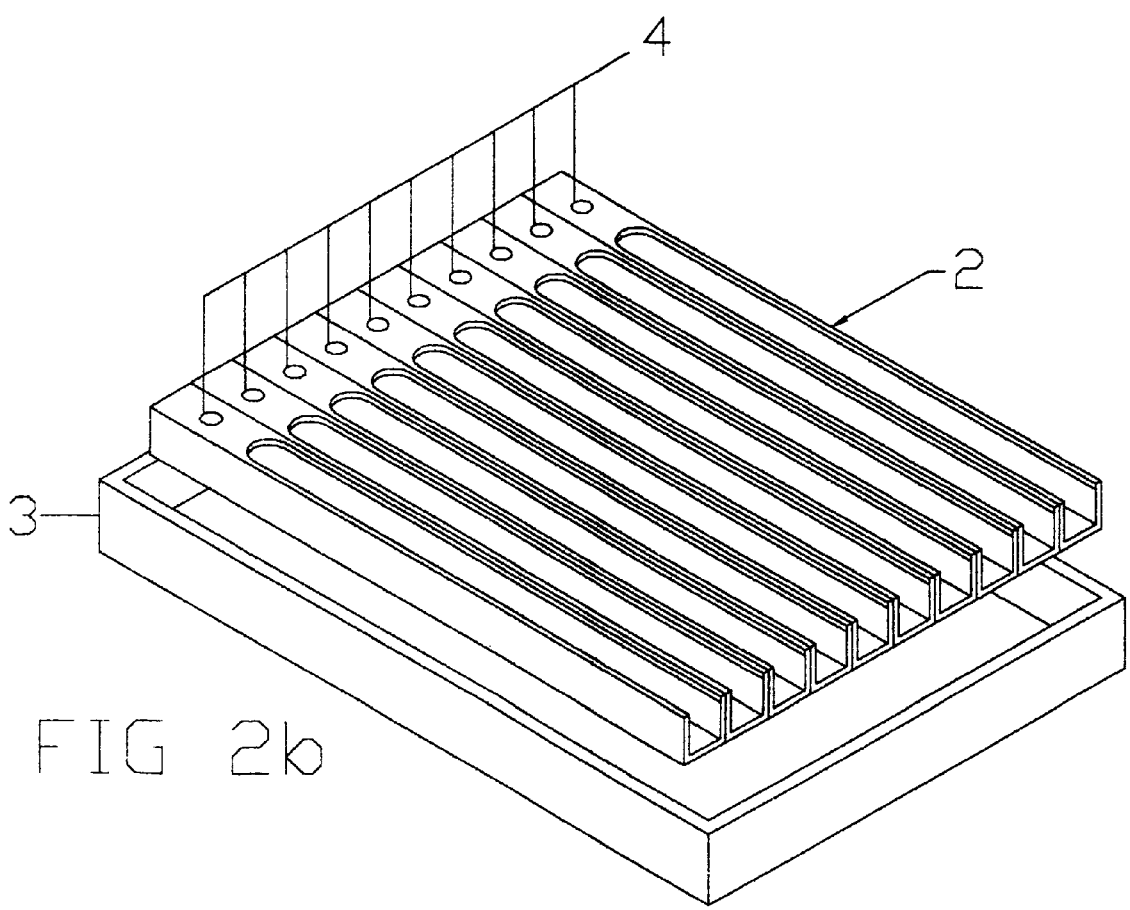
FIG. 2b is a perspective of a carrier assembly and base tray, preferred embodiment.
Figure 3:
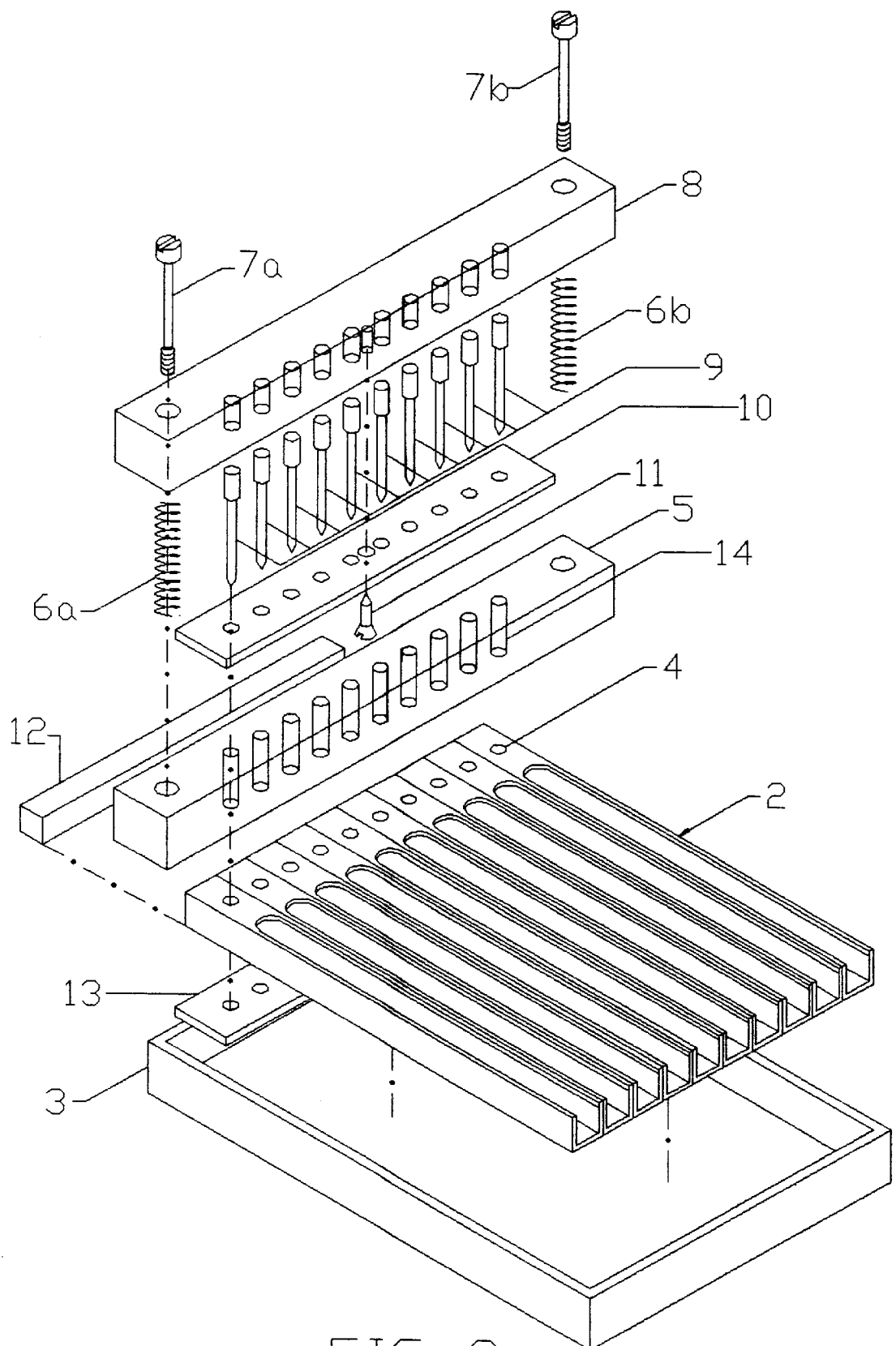
FIG. 3 is an exploded view of the machine, preferred embodiment.

In FIGS. 2, a and b, a predetermined length of square, hollow acrylic extrusion having a portion of its upper side removed and having apertures 4 aligned in its upper and lower sides constitutes a carrier 1. A number of carriers co-joined make up a carrier assembly 2 which fits into a base tray 3. In FIG. 3, needles 9 are specific lengths of solid stainless steel material having a sharp point at one end and having a butt of a somewhat larger diameter. A needle guide 5, made from a predetermined length of square, solid acrylic material, bearing perforations 14 is affixed to the upper surface of carrier assembly 2 in such manner that perforations 14 correspond with apertures 4 in carrier assembly 2. A handle 8, made from a similar length of square, solid acrylic material, and having along its underside a series of voids so positioned as to align with perforations 14 and being of a size to accept the butts of needles 9, is provided. Needles 9 are held captive by a keeper 10 and a screw 11. Handle 8 is suitably pierced and recessed near each end to contain and conceal bolts 7, [a and b]. Springs 6 [a and b] along with bolts 7 [a and b] constitute a spring-return means for handle 8. A safety plate 13, made from a length of acrylic sheet material and having holes so spaced as to align with apertures 4 and perforations 14 is provided. A segment stopper 12 and base tray 3, both made from of acrylic sheet material are provided.

A second embodiment of the present invention relates only to the method of construction and can be easily seen by the use of FIG. 3. Handle 8 is cast, or molded, around needles 9 and has molded openings and recesses for bolts 7 and springs 6. Keeper 10 and screw 12 are eliminated. Carrier assembly 2, needle guide 5, segment stopper 12, and safety plate 13 are cast or molded in a single piece. Base tray 3 is cast separately. Other than its having fewer parts and being quicker in production, this embodiment is identical in function and operation to the first embodiment.

ASSEMBLY AND OPERATION OF THE MACHINE

Needle guide 5, segment stopper 12, and safety plate 13 are welded to carrier assembly 2 in the relative positions indicated in FIG. 3. Needles 9 are inserted into handle 8, keeper 10 is installed over the shanks of needles 9 and is secured by screw 11. The handle assembly is then installed into the carrier and guide assembly by inserting all needles into their respective openings. Springs 6 [a and b] are put into position. Bolts 7 [a and b] are installed into their respective recesses in the handle and down through the longitudinal axes of springs 6 [a and b] and are then screwed into the carrier and guide assembly. The machine is set into base tray 3.

Assembly of the second embodiment, wherein several parts are molded as one, consists of simply attaching the handle assembly to the carrier and guide assembly by use of springs 6 [a and b] and bolts 7 [a and b], and setting the machine into base tray 3.

Operation of the machine is identical for either embodiment. Blood segments are placed into carrier assembly 2 and pushed fully forward. Handle 8 is pressed firmly downward and released. Perforated blood segments are then removed for processing as usual.

CONCLUSION

In conclusion, the present invention serves to open a number of blood segments quickly, cleanly, and simultaneously. The segments need not be manipulated in any special way as is the case with all other known methods of opening, and the position of the identification sticker is unimportant. Furthermore, the present invention is intended for very long-term use thereby reducing, to some degree, the amount of bio-hazardous material to be discarded.

While only one embodiment of the present invention has been shown and a second embodiment merely described, it is to be understood that many changes and modifications may be made thereunto, and that a combination of the two embodiments may be made, without departing from the spirit and scope of the invention as defined in the appended claims and their legal equivalents.

We claim:

1. A machine for piercing a plurality of blood segments simultaneously comprising:
   a. means for holding and aligning the plurality of blood segments individually and separately, said means for holding and aligning including aperture means for guiding a plurality of piercing devices therethrough;
   b. a member having affixed thereto said plurality of piercing devices corresponding to a number of aperture means in means for holding and aligning; and
   c. guide means for guiding said plurality of piercing devices through said aperture means to pierce said blood segments positioned in holding and aligning means, whereby actuation of said member causes said piercing devices to penetrate said blood segments.

2. The machine according to claim 1 wherein
   said means for holding and aligning including a plurality of carriers made of rigid, clear, plastic material, said carriers being laterally co-joined,
   said member including a handle made of rigid, clear plastic material bearing said plurality of piercing devices, and
   said guide means including a bar made of rigid, clear plastic material having therein a plurality of apertures corresponding to and being aligned with said number of aperture means in said holding and aligning means, whereby actuating said handle moves said piercing devices through said apertures of said guide means and aperture means of said holding and aligning means thereby penetrating said plurality of blood segments.

* * * * *